United States Patent [19]

Coelho, Jr.

[11] Patent Number: 5,429,624
[45] Date of Patent: Jul. 4, 1995

[54] FLUID DRAINAGE ELEMENT

[75] Inventor: Donald A. Coelho, Jr., Bellingham, Mass.

[73] Assignee: The Kendall Company, Mansfield, Mass.

[21] Appl. No.: 190,396

[22] Filed: Feb. 2, 1994

[51] Int. Cl.$^6$ ............................................. A61F 5/44
[52] U.S. Cl. ........................... 604/323; 128/DIG. 24
[58] Field of Search ............... 128/DIG. 24, 760; 604/322-326

[56] References Cited

U.S. PATENT DOCUMENTS

| | | | |
|---|---|---|---|
| 3,186,410 | 6/1965 | Buono | 604/324 |
| 3,332,422 | 7/1967 | Jinkens et al. | 604/325 |
| 3,537,109 | 11/1970 | Spurrier et al. | 604/325 |
| 3,943,929 | 3/1976 | Patel | 604/325 |
| 4,236,517 | 12/1980 | Langston et al. | 604/323 |
| 4,254,771 | 3/1981 | Vidal | |

Primary Examiner—Jerome L. Kruter
Attorney, Agent, or Firm—Alvin Isaacs

[57] ABSTRACT

The invention features a fluid drainage element which includes a housing having integral front and side walls and a back wall adapted to fit in fluid communication with a urine collection bag, the walls defining a chamber in the housing. The housing also contains a tubular section integral with the front wall, the tubular section including an inner wall defining a lumen which is in fluid communication with the chamber. The inner wall includes one or more ribs arranged circumferentially and shaped so as to maximize the cross-sectional area of the inner wall, act as an integral tubing stop, and additionally to promote capillary flow of fluid through the tubular section and into the chamber.

18 Claims, 3 Drawing Sheets

FLUID DRAINAGE ELEMENT

FIELD OF THE INVENTION

The invention relates to medical devices which facilitate drainage of a patient's bodily fluid.

BACKGROUND OF THE INVENTION

Drainage devices, such as urine receptacles or bags, are known for the collection of bodily fluids. These receptacles typically include walls defining a fluid collection space, and are adapted to connect to a drainage catheter leading from the patient's body. Often, during a drainage procedure, liquid accumulates at the junction of the tube and the collection bag, thus occluding or impeding the flow of fluid into the bag.

It is an object of the invention to promote unimpeded flow of fluid between a drainage tube and a fluid collection receptacle. It is another object of the invention to provide for faster flow and thus for flow of an increased volume of fluid in a fluid collection system. Yet another object is to provide for ease of fluid flow via increased capillary action within a drainage system. A still further object is to provide an integral tubing stop for facilitating manufacture of a fluid drainage system.

SUMMARY OF THE INVENTION

The invention features a fluid drainage element, comprising a housing having integral front and side walls and a back wall adapted to fit in fluid communication with a liquid collection bag. The walls define a chamber in the housing, and the housing also contains a tubular section integral with the front wall. The tubular section includes an inner wall defining a lumen which is in fluid communication with the chamber, the inner wall including one or more ribs arranged circumferentially and shaped so as to function as an integral tubing stop and promote capillary flow of fluid through the tubular section and into the chamber.

The fluid drainage element of the invention may act as an anti-reflux device. Alternatively, the element may serve the purpose of acting as an inlet port, i.e., with a relatively small housing and chamber, with the tubular section being directly connected in fluid communication with a fluid collection bag.

Preferably, each rib is arranged and shaped so as to increase the inner cross-sectional area of the lumen to promote the flow of an increased volume of fluid through the element.

Preferably, each rib acts as a stop during insertion of a drainage tube into the tubular section of the drainage element.

Each rib may be rectangularly shaped such that the long sides of the rectangle are parallel with the longitudinal axis of the tubular section, and the short sides form leading and trailing edges with respect to fluid flow through the element. The element will include at least one rib and preferably includes a plurality of ribs, e.g., two ribs, three ribs, four ribs, or more. The cross-sectional area of the rib-containing portion of the tubular extension is larger than the cross-sectional area of the portion of the tubular extension which does not contain ribs.

The tubular section, also having leading and trailing ends corresponding to the fluid entry and exit ends of the element, may terminate as a diagonal edge at its trailing end, with respect to the longitudinal axis of the tubular section. The one or more ribs terminate coextensive with the trailing end which is preferably diagonal.

The leading end of the tubular section may be adaptable to contain an insertable drainage tube, and the one or more ribs begin within the tubular section leading end and thus act as a stop for insertion of the drainage tube. Thus, the drainage tube, upon insertion, abuts the one or plural ribs, or sits sufficiently close thereto to promote capillary flow of fluid flowing through the element.

As used herein, where the drainage tube end is "sufficiently close" to the one or more ribs to promote capillary flow of fluid, the end of the drainage tube may abut the ribs or it may be within several millimeters, or even 1-2 centimeters of the ribs, depending upon the amount and type of density of the fluid flowing through the tube.

In other preferred embodiments, the element includes a conduit distal to the tubular section trailing end and providing fluid communication between the tubular section and the housing chamber, the conduit comprising a flowpath formed in part by the diagonal and a hole formed by a cut-away of the tubular section inner wall. The conduit thus re-orients the flow of fluid perpendicular with respect to the direction of fluid flow through the tubular section.

Preferably, the fluid drainage element is made of a semi-rigid material which is substantially transparent material.

The invention also features a fluid drainage system which includes the above-described fluid drainage element, a drainage tube having a trailing end, wherein the drainage tube trailing end is inserted within the tubular section so as to provide fluid communication therebetween, and a collection bag, wherein the fluid drainage element is affixed in fluid communication with the collection bag.

In preferred embodiments, the drainage tube trailing end is sealed within the tubular section via solvent bonding, and the drainage element is affixed to the collection bag via radio frequency (RF) welding.

The invention also features a fluid collection bag comprising front and back walls sealed together around their peripheries and adapted to be in fluid communication with a drainage tube, wherein the bag is shaped substantially square or rectangular.

Preferably, the front wall of the bag is made of a flexible substantially transparent material, and the back wall is made of a flexible substantially opaque material. The front wall of the bag may bear volumetric markings for visual assessment of the volume of fluid contained within the bag.

The invention also features a method of draining fluid, such as urine, from a patient. The method includes (a) connecting a drainage tube at its leading end through a catheter to a patient, wherein the drainage tube at its trailing end is in fluid communication with a fluid drainage element comprising a housing having integral front and side walls and a back wall adapted to fit in fluid communication with a liquid collection bag, the walls defining a chamber in the housing, the housing also containing a tubular section integral with the front wall, said tubular section comprising an inner wall defining a lumen which is in fluid communication with the chamber, the inner wall including one or more ribs arranged circumferentially on the inner wall and shaped so as to increase the volume and promote capillary flow of fluid through the tubular section and into the chamber, wherein the drainage tube trailing end is inserted within the tubular section sufficiently close to the one or more ribs to promote fluid capillary flow, and a collection bag, wherein the housing is affixed in fluid communication with the collection bag. The method also includes the step of (b) allowing fluid to flow from the patient through the drainage tube, tubular section, and housing and into the collection bag.

Further features will become more fully apparent in the following description of the embodiments of this invention and from the appended claims.

DETAILED DESCRIPTION OF THE INVENTION

Figure 1:
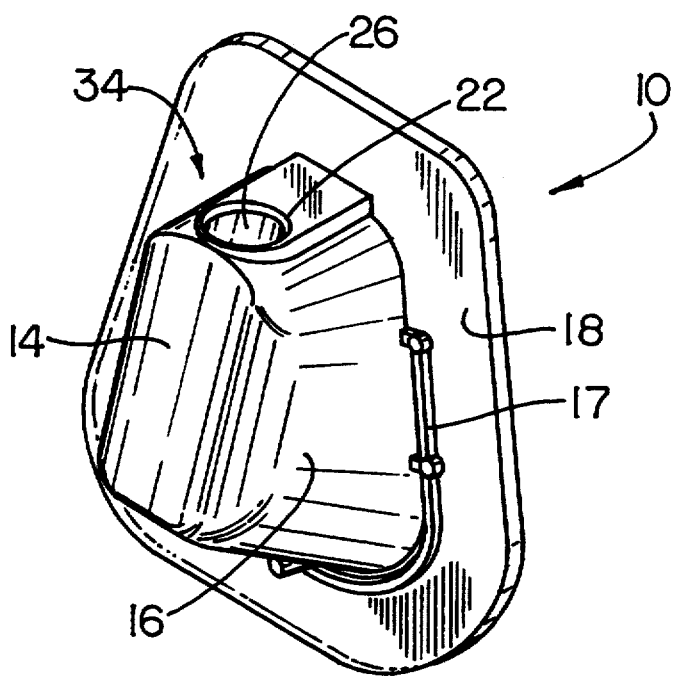
FIG. 1 is an elevated perspective view of the fluid drainage element of the invention.
Figure 2:
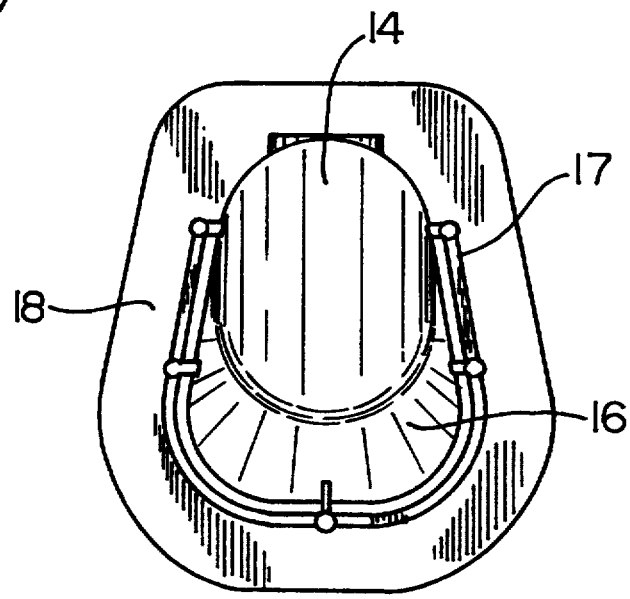
FIG. 2 is front end view of the fluid drainage element of the invention.
Figure 3:
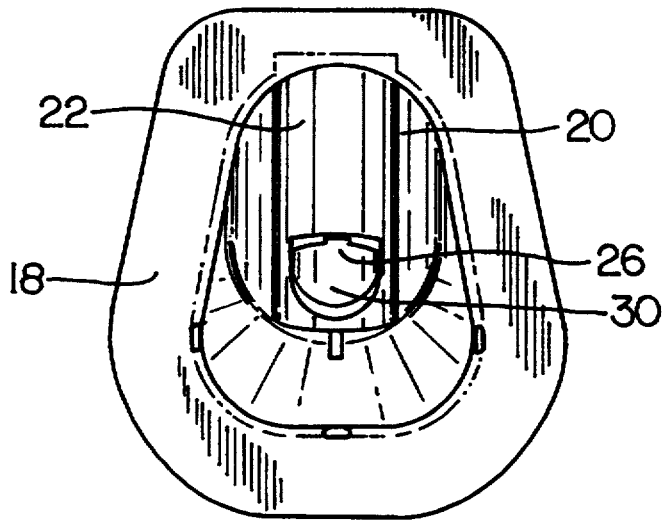
FIG. 3 is a back end view of the fluid drainage element of the invention.

Referring to FIGS. 1–8, an improved anti-reflux element is shown. The fluid drainage element of the invention 10 is an integral piece, including a housing having front and side walls 14,16, respectively, defining an anti-reflux chamber 20 and a tubular section 22 integral with the front wall 14 and positioned within chamber 20. The front and side walls of element 10 are continuous and form a cup, the open lip of the cup being integral with a platform 18, the underside of the cup thus being substantially open (FIG. 3) for establishing fluid communication with a collection bag. The drainage element is adapted to affix to a fluid collection receptacle 38 (FIG. 8) via the underside of element 10 at platform 18, much of the remainder of the platform 18 being cut away for adaptation of the element to a collection bag. Where the side wall 16 of element 10 joins platform 18, ridge 17 is formed to provide structural integrity to the element 10. The element is also adapted to connect to a drainage tube 42 via the tubular section.

Figure 4:
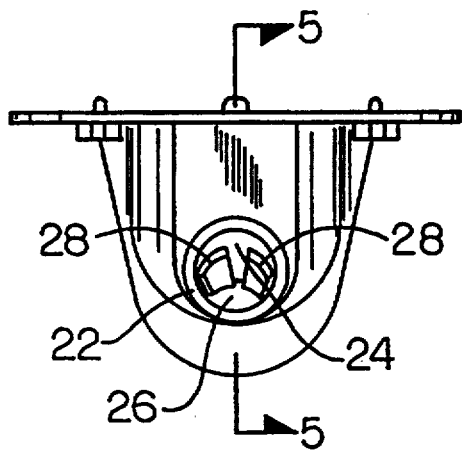
FIG. 4 is a bottom end view of the fluid drainage element of the invention.
Figure 5:
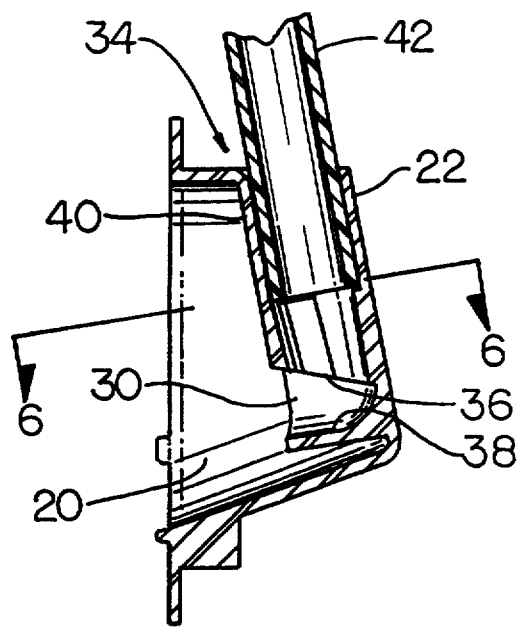
FIG. 5 is a cross-sectional view of the fluid drainage element of the invention along line 5/5 of FIG. 4.

Referring particularly to FIGS. 4–7, the tubular section 22 of the element 10 is formed by an annular inner wall or septum 40 having an inner surface 24 defining a lumen 26. Tubular section 22 has a leading end 34 and a trailing end 36, the leading end coinciding with the drainage tube-insertion end of the drainage element 10, and the trailing end 36 terminating as a diagonal cut-away. For ease of interpretation of the text and drawings, a leading end of any component of the fluid drainage element of the invention, or a fluid drainage system as described herein, is the end into which fluid is introduced during flow from the body to the collection bag, and a trailing end of a component is the end from which fluid leaves that component and flows into the next component. Thus, the tubular section trailing end is diagonal with respect to the longitudinal axis of the tubular section. The lumen 26 of tubular section 22 is in fluid communication with the chamber 20 via conduit 30, as is evident in FIG. 5, in which the tube is illustrated inserted into tubular section 22. FIG. 5 also shows how conduit 30 re-orients the flow of fluid so that the flow becomes perpendicular in conduit 30 with respect to flow through tubular section 22. Conduit 30 is formed in part by the diagonal trailing end 36, wall 38, and by a cut-out of the trailing end of septum 40 of tubular section 22.

It is also contemplated that the cup may be considerably smaller than as depicted in the figures, i.e., the tubular section 22 may attach to a fluid collection bag via a cup which allows conduit 30 to lead directly to the bag, thus tubular section 22 may function primarily as an inlet port for flow of fluid from a drainage tube into a collection bag.

Referring again to FIGS. 4–7, the inner surface 24 of tubular section 22 includes plural ribs or projections 28 extending circumferentially around the tubular section inner surface 24. The ribs alternate with flutes 29, i.e., a flute being identical with the inner surface 24 of tubular section 22 between each two adjacent ribs 28 and being a depressed surface with respect to the lumen surface of the projecting ribs. The alternating ribs and flutes are of a size, shape, and arrangement so as to promote capillary flow of fluid through the tubular section 22 and into the chamber 20, and to increase the volume of fluid which flows through section 22. That is, as shown in cross-section in FIG. 6, the presence of the alternating ribs and flutes provides for increased cross-sectional area of the inner wall of the tubular section, which allows for flow of an increased volume of fluid through the lumen. During capillary flow, fluid is first pulled from an inserted drainage tube onto the intersection of the rib projections and the flutes, where it is then wicked into conduit 30.

Each rib 28 is of a generally square or rectangular shape, with the long side of the rectangle extending along the longitudinal axis of the tubular section 22. For purposes of description, the leading end of each rib is oriented towards the proximal end 34 of the tubular section 22, and the trailing end of each rib is oriented towards the trailing end of tubular section 22. The ribs 28 do not extend the full length of tubular section 22, as shown in FIGS. 4 and 5. The size and spacing of the ribs around the tubular section inner surface is intended to provide for increased cross-sectional area in the tubular section and to maximize capillary flow. The one or more ribs also prevents the accumulation of fluid in the drainage element to the extent that it inhibits or prevents fluid drainage from a drainage tube into a collection bag.

Figure 6:
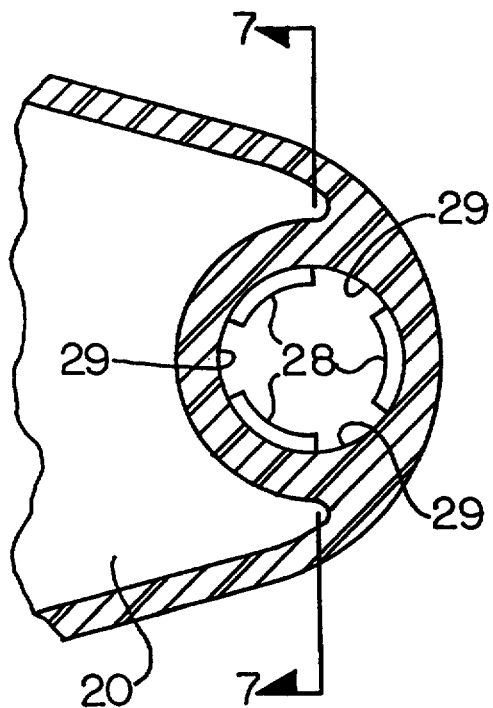
FIG. 6 is a cross-sectional view of the fluid drainage element of the invention along line 6/6 of FIG. 5.
Figure 7:
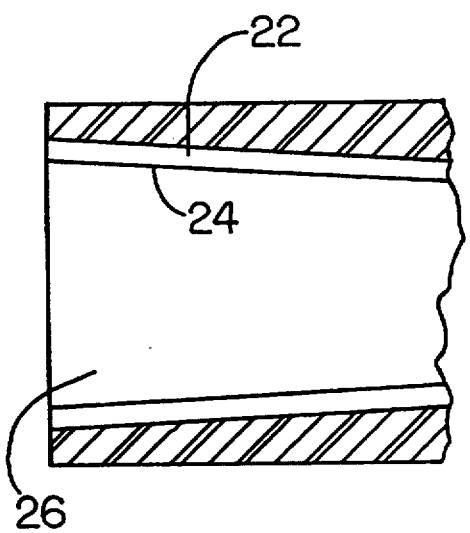
FIG. 7 is a cross-sectional view of the fluid drainage element of the invention along line 7/7 of FIG. 6.
Figure 8:
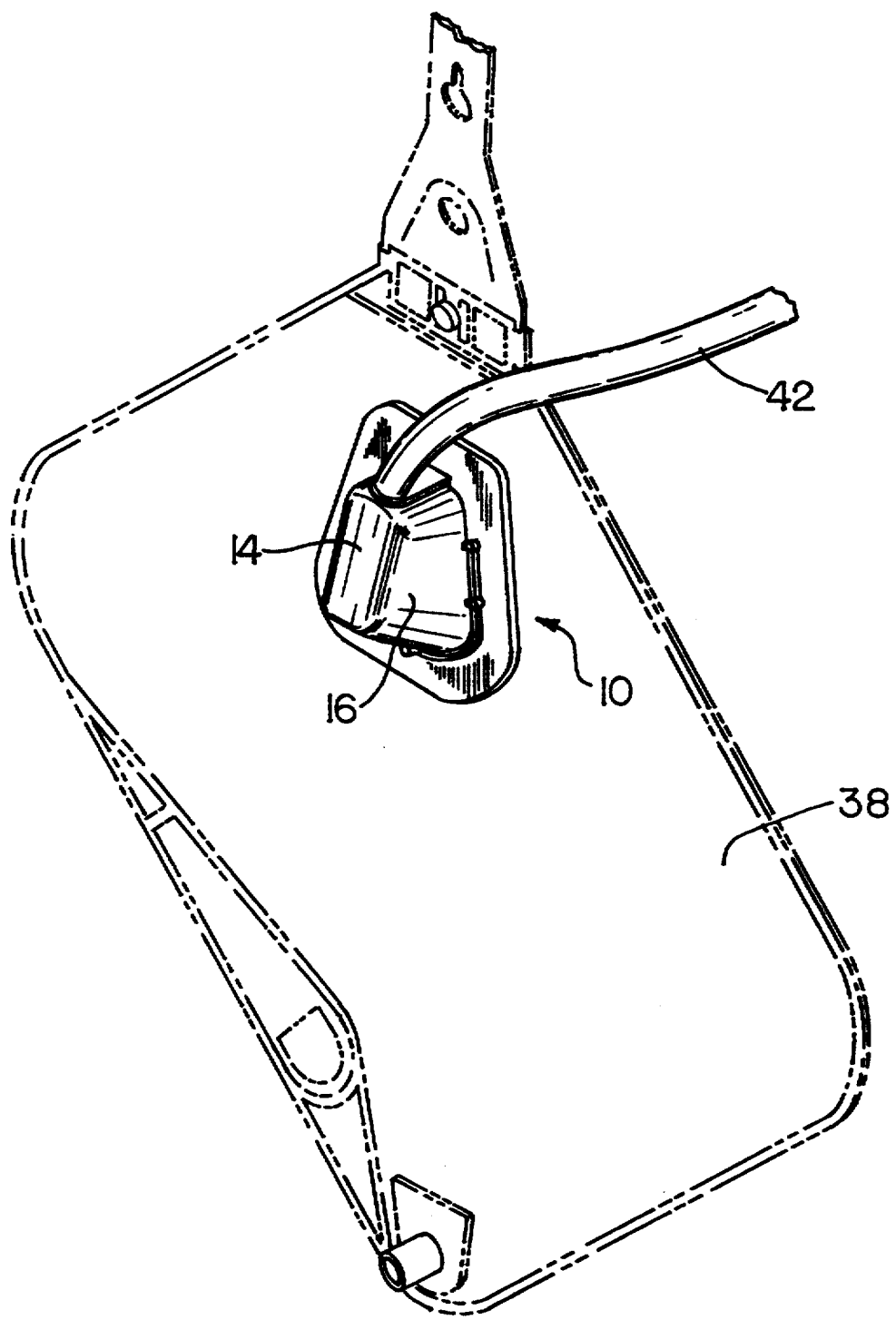
FIG. 8 is an elevated perspective view of the fluid drainage element of the invention fitted with a fluid collection receptacle and drainage tube.

Referring to FIGS. 5 and 6, in which tubular section 22 is shown in longitudinal and lateral cross-sections, it can be seen that the cross-sectional area of the inner wall of tubular section 22 is larger in the ribbed portion of the tubular section, i.e., the trailing end, and relatively smaller in the unribbed leading end 34 of tubular section 22. When the drainage tube 42 is in place, it is inserted and fits tightly within the leading end 34 of the tubular section 22, and abuts the leading ends of the ribs (FIG. 5). Ribs 28 project outwardly from the tubular inner surface 24 toward the center of lumen 26 far enough to prevent a drainage tube from pushing further into tubular section 22 than the leading end of the ribs.

Although a single rib is sufficient to provide the advantages of increased fluid volume and capillary flow through the element, in a preferred embodiment, there are three ribs extending from the tube inner surface, spaced approximately at equidistances circumferentially around the tubular section inner surface. Alternatively, there may be four, five or more ribs.

At the diagonal trailing end 36 of tubular section 22, as shown in FIG. 5, the trailing end of each rib 28 terminates coextensive with that diagonal. The diagonal end 36 promotes the flow of fluid from the tubular section into conduit 30, and thence into chamber 20 and the collection bag.

The drainage element of the invention is made by injection or insert molding using any material which will harden to form a semi-rigid impermeable material, e.g., a plastic, e.g., polyvinylchloride. Typically, this material will be transparent so as to enable observation of fluid flow through the element. The ribs are generally formed at an angle of between 20 and 120 degrees with respect to the surface of the inner wall 24 of tubular section 22. Preferably, this angle will be at least 45 degrees, and most preferably on the order of 90 degrees. Similarly, the leading end of each rib, i.e., the end that abuts an inserted drainage tube, is formed at an angle of between 45 and 90 degrees with respect to the inner surface 24 of tubular section 22. The drainage end of a drainage tube is inserted into the tubular section 22 until it abuts against the ribs 28, and may then be solvent bonded at its edges within the element, e.g., using cyclohexane. If the drainage tube does not abut ribs 28, the distance between the end of the tube and the ribs must be close enough to promote capillary fluid flow through tubular section 22. The element is then affixed to a collection bag by heat bonding, e.g., RF bonding.

The fluid collection bag includes front and back walls sealed together around their peripheries and adapted to be in fluid communication with the drainage tube using the element described herein. The bag itself is shaped substantially square or rectangular. The front wall may be cut from a sheet of flexible substantially transparent material and the back wall cut from a flexible substantially opaque material. Thus, multiple bags may be cut from a single sheet of front or back wall material without wasting the intervening material, as occurs in fabricating round bags. Once cut, the front and back wall pieces are bonded together at the periphery, e.g., heat-bonded.

When the element of the invention is used as an anti-reflux chamber, the element may be attached to the collection bag through a hole in the front wall of the bag that is sized with respect to the chamber so as to enhance the anti-reflux property. That is, the hole in the front wall of the collection bag may be smaller than the corresponding opening on the underside of the drainage element, i.e., the open face of the cup. Thus, when the element is affixed to the front wall of the collection bag so as to cover the hole in the bag, the hole corresponds to only about one-third to one-half of the open area on the underside of element 10. The hole in the collection bag may be positioned opposite conduit 30. The reduced-sized hole enhances the anti-reflux property of element 10 by reducing the opportunity for fluid in the bag to flow back into chamber 20, particularly during movement of the bag.

In use, with the drainage tube and collection bag in place, fluid flows from the draining end of the drainage tube and into the drainage element. As fluid leaves the drainage tube, it is pulled out of the drainage tube and into the tubular section 22 of the drainage element 10 via capillary action and increased volume flow. The circumferential arrangement of alternating ribs and flutes around the inner surface of tubular section 22 breaks fluid surface tension which may build up along the cross-sectional plane within the tubular section 22, and thus reduces or prevents the accumulation of fluid within the element 10. At the same time, the arrangement of alternating ribs and flutes promotes the flow of an increased volume of fluid through the element 10. This arrangement also inhibits the formation of a fluid block or an airlock in the element 10 which may prevent fluid drainage into the collection bag. Once the fluid reaches conduit 30, it is carried into chamber 20 and then into the collection bag.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

I claim:

1. A fluid drainage system, comprising
a fluid drainage element comprising:
a housing having integral front and side walls and a back wall adapted to fit in fluid communication with a liquid collection bag, said walls defining a chamber in the housing, said housing also containing a tubular section integral with said front wall, said tubular section comprising an inner wall defining a lumen which is in fluid communication with said chamber, said inner wall including a rib extending from said inner wall into said lumen and shaped so as to function as an integral tubing stop and promote capillary flow of said fluid through said tubular section and into said chamber;
a drainage tube having a trailing end, wherein said drainage tube trailing end is inserted within said tubular section so as to provide fluid communication therebetween; and
a collection bag, wherein said fluid drainage element is affixed in fluid communication with said collection bag.

2. The fluid drainage element of claim 1 wherein said inner wall includes a plurality of ribs arranged circumferentially on said inner wall.

3. The fluid drainage element of claim 1 or 2 wherein each said rib is rectangularly shaped such that the long sides of the rectangle are parallel with the longitudinal axis of said tubular section.

4. The fluid drainage element of claim 2, said plural ribs comprising at least two ribs.

5. The fluid drainage element of claim 4, said plural ribs comprising three ribs.

6. The fluid drainage element of claim 1 or 2 wherein each said one or plural ribs is formed at an angle on the order of 90 degrees relative to the surface of said inner wall.

7. The fluid drainage element of claim 1, wherein said housing comprises a semi-rigid material.

8. The fluid drainage element of claim 7, said semi-rigid material being substantially transparent.

9. The fluid drainage system of claim 1, wherein said drainage tube trailing end is sealed within said tubular section via solvent bonding.

10. The fluid drainage system of claim 1 wherein said drainage element is affixed to said collection bag via solvent bonding.

11. A fluid drainage element, comprising:

a housing having integral front and side walls and a back wall adapted to fit in fluid communication with a liquid collection bag, said walls defining a chamber in the housing, said housing also containing a tubular section integral with said front wall, said tubular section comprising an inner wall defining a lumen which is in fluid communication with said chamber, said inner wall including a rib extending from said inner wall into said lumen and shaped so as to function as an integral tubing stop and promote capillary flow of said fluid through said tubular section and into said chamber, said tubular section includes a leading end and a trailing end, said leading end being adaptable to contain an insertable drainage tube and said trailing end terminating at a diagonal, wherein said plural ribs terminate coextensive with said trailing end diagonal.

12. The fluid drainage element of claim 11, wherein said plural ribs begin within said tubular section leading end, and said tubular section leading end includes a smaller inner cross-sectional area than the inner cross-sectional area of said tubular section trailing end such that said insertable drainage tube, upon insertion, abuts said rib, the tubular section of the rib-containing portion having a cross-sectional area which is larger than the cross-sectional area of the portion of the tubular section which does not contain ribs.

13. The fluid drainage element of claim 11 wherein said inner wall includes a plurality of ribs arranged circumferentially on said inner wall.

14. The fluid drainage element of claim 11 wherein each said rib is rectangularly shaped such that the long sides of the rectangle are parallel with the longitudinal axis of said tubular section.

15. The fluid drainage element of claim 14, said plural ribs comprising at least two ribs.

16. The fluid drainage element of claim 14, said plural ribs comprising three ribs.

17. The fluid drainage element of claim 11 wherein each said one or plural ribs is formed at an angle on the order of 90 degrees relative to the surface of said inner wall.

18. A fluid drainage element, comprising:

a housing having integral front and side walls and a back wall adapted to fit in fluid communication with a liquid collection bag, said walls defining a chamber in the housing, said housing also containing a tubular section integral with said front wall, said tubular section comprising an inner wall defining a lumen which is in fluid communication with said chamber, said inner wall including a rib extending from said inner wall into said lumen and shaped so as to function as an integral tubing stop and promote capillary flow of said fluid through said tubular section and into said chamber, said tubular section includes a leading end and a trailing end, said leading end being adaptable to contain an insertable drainage tube and said trailing end terminating at a diagonal, wherein said plural ribs terminate coextensive with said trailing end diagonal; and a conduit distal to said tubular section trailing end and providing fluid communication between said tubular section and said housing chamber, said conduit comprising a space formed in part by said diagonal and a hole formed by a cut-away of said tubular section inner wall.

* * * * *